(12) United States Patent
Pinchuk et al.

(10) Patent No.: US 6,254,633 B1
(45) Date of Patent: Jul. 3, 2001

(54) DELIVERY DEVICE FOR A MEDICAL DEVICE HAVING A CONSTRICTED REGION

(75) Inventors: Leonard Pinchuk; John B. Martin, Jr., both of Miami, FL (US)

(73) Assignee: Corvita Corporation, Miami, FL (US)

( * ) Notice: Subject to any disclaimer, the term of this patent is extended or adjusted under 35 U.S.C. 154(b) by 0 days.

(21) Appl. No.: 08/989,119

(22) Filed: Dec. 11, 1997

Related U.S. Application Data (60) Provisional application No. 60/040,062, filed on Feb. 12, 1997.

(51) Int. Cl.$^7$ .......................................... A61F 2/00
(52) U.S. Cl. .............................. 623/1.3; 606/200
(58) Field of Search .................... 606/191, 194, 606/195, 198, 200; 623/1, 1.3, 1.13, 1.31

(56) References Cited

U.S. PATENT DOCUMENTS

| | | | |
|---|---|---|---|
| 4,130,119 | * 12/1978 | Sessions et al. | 606/195 |
| 4,705,517 | 11/1987 | DiPisa, Jr. | 623/12 |
| 4,793,348 | * 12/1988 | Palmaz | 606/194 |
| 5,026,377 | 6/1991 | Burton et al. | |
| 5,201,757 | * 4/1993 | Heyn et al. | 606/200 |
| 5,382,261 | 1/1995 | Palmaz | 606/158 |
| 5,484,444 | 1/1996 | Braunschweiler et al. | |
| 5,626,605 | * 5/1997 | Irie et al. | 606/200 |
| 5,681,347 | * 10/1997 | Cathcart et al. | 606/200 |
| 5,695,519 | * 12/1997 | Summers et al. | 606/200 |
| 5,941,896 | * 8/1999 | Kerr | 606/200 |
| 6,022,336 | * 2/2000 | Zadno-Azizi et al. | 604/96 |

FOREIGN PATENT DOCUMENTS

| | | |
|---|---|---|
| 92 05 797 U | 7/1992 | (DE). |
| WO 95/32018 | 11/1995 | (WO). |
| WO 96/01591 | 1/1996 | (WO). |

* cited by examiner

*Primary Examiner*—Michael Milano
(74) *Attorney, Agent, or Firm*—Faegre & Benson (57) ABSTRACT

A delivery device for delivering an implantable, radially expandable medical device having a constricted region for occluding fluid flow to a desired location in a body lumen. The delivery device includes an outer sleeve, an inner tube terminating at its distal end in a plunger, and a tapered guide member. In one embodiment, the tapered guide member is attached to and extends away from the constricted region of the occlusion device, and is thus implanted in the body lumen along with the occlusion device upon deployment of the occlusion device at the desired treatment location. In a second embodiment, the tapered guide member is integrated into the constricted region of the occlusion device. In a third embodiment, an inflatable balloon is positioned distally of the medical device, and when inflated provides a tapered guide surface that eases the navigation of the delivery device through the body lumen. Upon deployment of the medical device at the desired location, the balloon is deflated to such a size as to be able to be withdrawn through the constricted region of the occlusion device, and is thus removed from the body lumen.

6 Claims, 7 Drawing Sheets

DELIVERY DEVICE FOR A MEDICAL DEVICE HAVING A CONSTRICTED REGION

This application claims the benefit of U.S. Provisional Application No. 60/040,062 filed Feb. 12, 1997.

TECHNICAL FIELD

The present invention relates generally to delivery devices of the type for delivering an implantable medical device to a desired location in a body lumen and deploying the medical device at the desired location. In particular, the present invention is a delivery device that is adapted for use with a radially expandable medical device having a constricted region.

BACKGROUND OF THE INVENTION

Medical devices adapted for implantation into body lumens that support fluid flow are well known and commercially available. One such device is the self-expandable stent of the type disclosed in the Wallsten U.S. Pat. No. 4,655,771. Stents of this type can be used to treat vascular stenosis and to maintain openings in the urinary, bilary, esophageal, tracheal and bronchial tracts of a patient. Self-expanding stents are generally comprised of a plurality of resilient filaments that are helically wound and interwoven to form a porous lattice. The stents assume a generally tubular form having a first diameter in an unloaded state, but can be forced into a reduced-diameter, extended length form (i.e. the "loaded" state) by inwardly-directed radial forces.

Another type of medical device adapted for implantation into a body lumen is an occlusion device designed to occlude a body lumen and thus stop fluid flow though the body lumen. One such occlusion device is described in the commonly assigned and co-pending U.S. patent application Ser. No. 08/797,983, which is expressly incorporated herein by reference in its entirety for all purposes. Occlusion devices of this type can be used to control internal bleeding, bypass a lumen, relieve the pressure created by an aneurysm in a lumen, or stop the flow of fluid to a tumor in a lumen.

Occlusion devices of the type shown and disclosed in application Ser. No. 08/797,983 are comprised of a self-expandable support structure and a flexible fluid flow-occluding membrane attached to the support structure. The support structure can be formed from any self-expanding means, including a number of filaments that are interwoven in a manner similar to that described in the Wallsten U.S. Pat. No. 4,655,771. Alternatively, the support structure can be comprised of etched or machined self-expanding tubes formed from nitinol or spring steel, such as those marketed under the tradename "Symphony" from MediTech, or other designs utilizing a plurality of zig-zag formed spring steels and the like. The membrane can be interwoven with at least portions of the support structure, or it can be formed separately from the support structure and attached to a portion of the interior or exterior surface of the support structure. The membrane can be fabricated from a microporous or non-porous material. Similar to self-expanding stents, the occlusion device assumes a substantially tubular shape in an unloaded, expanded state, and can be forced into a reduceddiameter, extended-length shape when subjected to inwardly directed radial forces. The occlusion device further includes a constricted region, which can be formed in either the membrane alone or in both the membrane and the support structure. The constricted region of the occlusion device is "closed" to fluid flow, and in this manner, the device occludes the lumen in which the occlusion device is implanted to restrict fluid flow through the lumen.

Methods for implanting medical devices in a body lumen are also known. A delivery system having proximal and distal ends and comprising an outer sheath, an inner catheter having a pointed tip, and a plunger is often used to deploy a self-expanding stent at the desired treatment location in a body lumen. The stent is compressed into its reduced-diameter state, and is held in its compressed state at the end of the inner catheter between the pointed tip and the plunger by the outer sheath of the delivery system. Such a delivery system can be inserted into a body lumen and tracked radiographically by monitoring the position of a radiopaque marker positioned on the outer sheath to guide the delivery system to the desired treatment location. As the system is guided through the lumen, the pointed tip of the inner catheter expands the body lumen in advance of the delivery system to ease navigation. A guide wire that extends through the inner catheter along the length of the outer sheath can also be used to aid in moving the delivery system through the lumen. When positioned at the treatment site, the stent is deployed by retracting the outer sheath, which releases the stent and allows it to self expand and engage the body lumen. After the outer sheath has been retracted and the stent is fully expanded, the inner catheter and pointed tip can be withdrawn back through the interior of the stent.

Such a delivery system can be difficult to use with occlusion devices such as those described above, however. Because such occlusion devices include a constricted region, it is difficult to withdraw the inner catheter and pointed tip through the constricted region when the occlusion device has been deployed at the treatment site. A delivery system having an outer sheath and a plunger without an inner catheter and pointed tip (i.e. an "open" delivery system) can more efficiently be used to deploy such a medical device. An open delivery system, however, may encounter difficulty in navigating the body lumen due to the tortuous nature of lumens. It is thus highly desirable to include a tip or a guide member that dilates the body lumen at the distal end of a delivery system used to deliver and deploy a medical device having a constricted region. A need therefore exists for an improved medical device delivery system that includes a guide member for dilating body lumens, yet is capable of being efficiently used with medical devices having a constricted region.

SUMMARY OF THE INVENTION

The present invention is a combination medical device and delivery device for delivering and implanting the medical device at a desired location in a body lumen. The medical device is of the type having a proximal end and a constricted region. The delivery device includes an outer sheath that encompasses the medical device at a distal end of the outer sheath. A manifold is attached to a proximal end of the outer sheath, and an inner tube that is coupled to the manifold is positioned within the outer sheath. The inner tube terminates in an end adjacent the proximal end of the medical device in the outer sheath.

In a first embodiment, the delivery device further includes a guide member that is attached to a distal end of the medical device. The guide member extends beyond the distal end of the outer sheath, and is adapted to guide the delivery device as it is advanced in a body lumen. The end of the inner tube engages the proximal end of the medical device to permit the retraction of the outer sheath at the desired location in the body lumen. In this manner, the medical device is deployed and implanted. The guide member of this first embodiment can include a dilator tip that is attached to and extends away from the tip of the constricted region of the medical device.

Alternatively, the dilator tip can be attached to and be coincident with at least a portion of the constricted region of the medical device.

In a second embodiment of the present invention, the delivery device includes a guide member and an inflation tube adapted to receive and carry a fluid flow. The inflation tube is positioned within the outer sheath of the delivery device. The guide member of this second embodiment includes an inflatable balloon fluidly coupled to the inflation tube. The balloon is inflated to provide a surface that is adapted to guide the delivery device through the body lumen as the delivery device is advanced at the lumen. The medical device can be deployed by retracting the outer sheath. The balloon can be deflated and withdrawn through the constricted region of the medical device after the medical device is deployed and implanted.

DETAILED DESCRIPTION OF THE INVENTION

Figure 1:
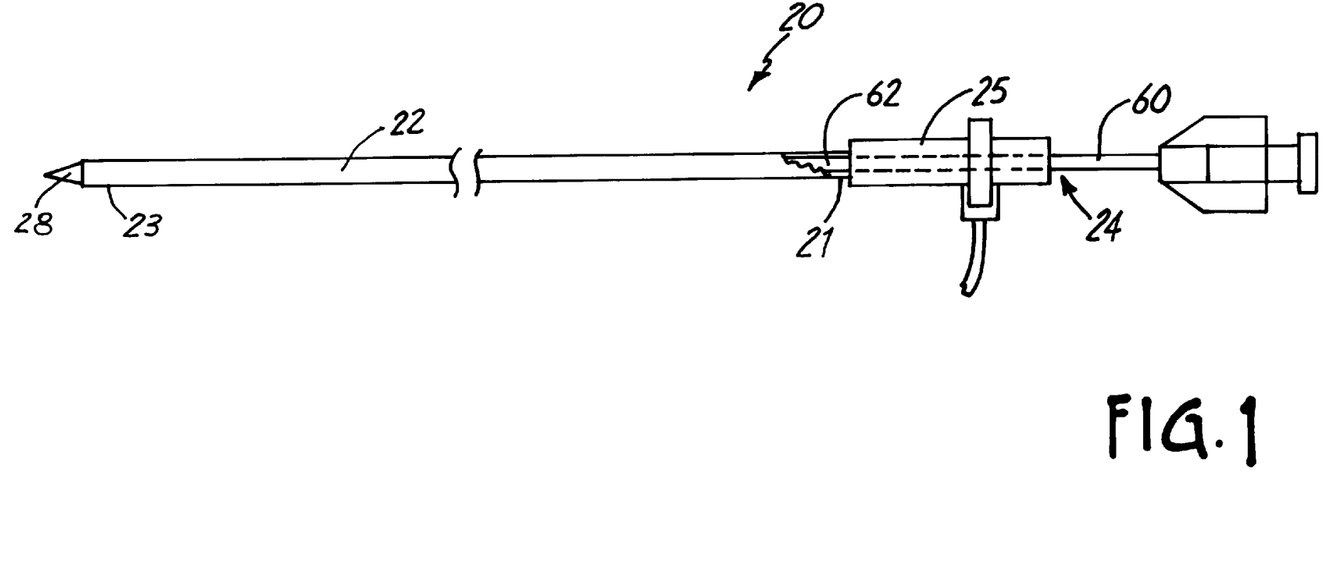
FIG. 1 is a side view of a delivery device in accordance with the present invention.

FIG. 1 is an illustration of a delivery device 20 in accordance with the present invention. Delivery device 20 is comprised of a flexible outer sheath 22 having a proximal end 21 and a distal end 23, an inner tube 24, and a manifold 25 coupled to the proximal end 21 of outer sheath 22. Inner tube 24 includes a rigid portion 60 and a flexible portion 62, the rigid portion 60 being bonded to the flexible portion 62 in any conventional manner such as by using adhesive. The rigid portion 60 and flexible portion 62 of inner tube 24 are adapted to extend into manifold 25, and outer sheath 22 surrounds the flexible portion of inner tube 24 in a coaxial fashion. The flexible portion 62 terminates at the distal end of inner tube 24 in a deployment member, such as a plunger (not visible in FIG. 1). A guide member 28 is positioned within outer sheath 22 distally of inner tube 24, and guide member 28 extends beyond the distal end 23 of outer sheath 22 to ease navigation through a body lumen by delivery device 20. As described in greater detail below, delivery device 20 is used to deliver and implant a medical device having a constricted region at a desired location within a body lumen.

Figure 2:
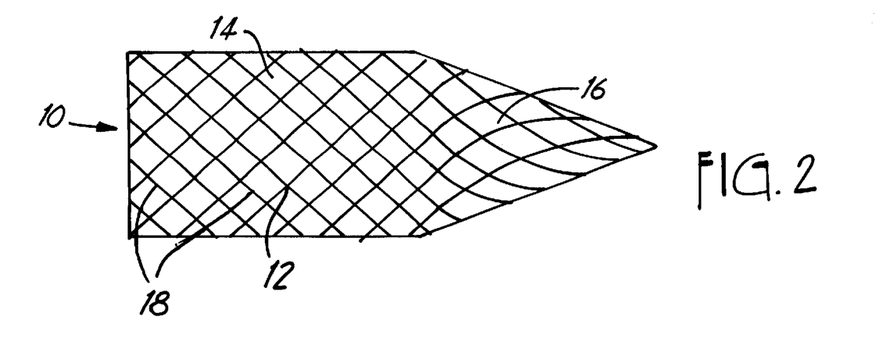
FIGS. 2–4 are side views of three different embodiments of medical devices for which the present invention is particularly suited.
Figure 3:
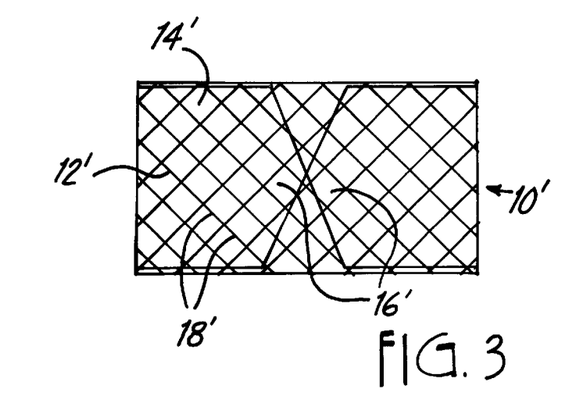
Figure 4:
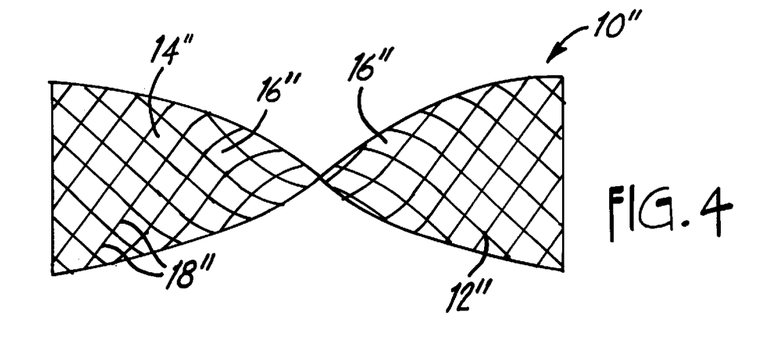

FIGS. 2–4 show three medical devices which can be deployed by the present invention. Specifically, FIGS. 2–4 show different embodiments of an occlusion device having a constricted region for occluding fluid flow in a body lumen, each of which is described in detail in the aforementioned co-pending and commonly assigned U.S. patent application Ser. No. 08/797,983. FIG. 2 shows an occlusion device 10 having a support structure 12 and a flexible fluid flow-occluding membrane 14. Support structure 12 is comprised of a plurality of elongated filaments 18 that are interbraided to form a collapsible and self-expanding structure 12. Support structure 12 can alternatively be formed from other self-expanding means, including self-expanding tubes formed from nitinol or spring steel, or other designs utilizing a plurality of zig-zag formed spring steels and the like. Fluid flow-occluding membrane 14 is positioned within and circumferentially engages support structure 12. Membrane 14 can be formed from a micro-porous or a non-porous material, and can be comprised of a plurality of filaments that are interwoven with the support structure 12. Materials well-suited for membrane 14 include polyurethane, silicone rubber, polyolefin, expanded polytetrafluoroethylene, or polymers generally known as hydrogels such as poly(2-hydroxyethyl methacrylate), polyacrylamide, and the like. The membrane 14 can include eluting or attached drugs such as antibiotics, bacteriostats, drugs generally denoted as chemotherapy drugs, drugs or particles emitting actinic radiation, drugs which promote blood clotting such as protamine, and the like, and combinations of the above. A preferred material for membrane 14 is polycarbonate urethane. Occlusion device 10 includes a constricted region 16 at an end of device 10, the constricted region 16 being substantially "closed" to occlude fluid flow in the body lumen in which occlusion device 10 is implanted. In the embodiment shown in FIG. 2, constricted region 16 is formed in both the support structure 12 and the fluid flow-occluding membrane 14.

FIG. 3 shows a second embodiment 10' of an occlusion device. The individual features of occlusion device 10' are similar to those shown in FIG. 2 and described above, and the same reference numbers followed by the prime (') symbol are used to indicate such features. Constricted region 16' of occlusion device 10' is positioned between the ends of occlusion device 10', and constricted region 16' is formed solely in membrane 14'.

FIG. 4 shows a third embodiment 10" of an occlusion device. The individual features of occlusion device 10" are similar to those shown in FIGS. 2 and 3 and described above, and the same reference numbers followed by the double prime (") symbol are used to indicate such features. In the embodiment shown in FIG. 4, constricted region 16" of occlusion device 10" constricts both the support structure 12" and the membrane 14" between the ends of occlusion device 10".

The occlusion devices shown in FIGS. 2–4 are representative of the types of medical devices that are suited for use with the present invention. Other medical devices having a constricted region and a support structure can also be used with the present invention.

Figure 6:
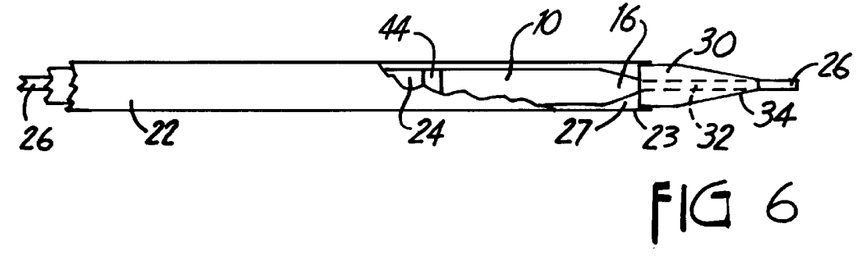
FIGS. 6–8 are side views of a first embodiment of the present invention in the various stages of deploying the medical device shown in FIG. 4.
Figure 7:
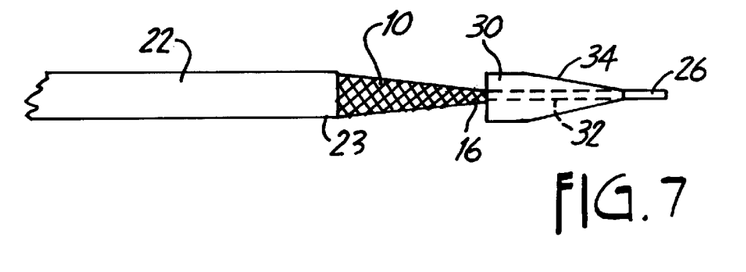
Figure 8:
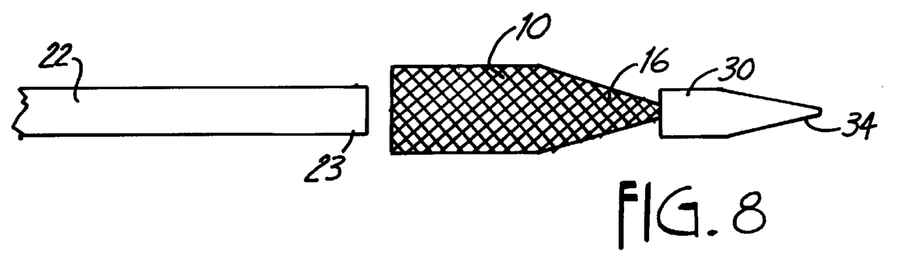

Turning now to FIGS. 6–8, a distal portion of the delivery device 20 of FIG. 1 and discussed above is shown in the various stages of deploying occlusion device 10 of FIG. 2. Occlusion device 10 is carried within outer sheath 22 in a collapsed condition. Specifically, occlusion device 10 is carried within outer sheath 22 with the occlusion device 10 at a medical device encompassing region 27 distally of plunger 44, which, as described above, is a deployment member positioned at the distal end of inner tube 24. Guide member 28 of delivery device 20 includes a dilator tip 30, which extends from the distal end 23 of outer sheath 22. Dilator tip 30 has a tapered surface 34 that is adapted to dilate a body lumen and guide the delivery device through the lumen as the delivery device 20 is advanced in the body lumen in the manner described below. Dilator tip 30 is preferably conical, although other shapes having a surface that dilates a lumen as delivery device 20 is advanced in the lumen can of course be used. Dilator tip 30 can include a guide wire passage 32 (shown in phantom in FIGS. 6 and 7). A guide wire 26 can be inserted through an axial lumen in inner tube 24 and through guide wire passage 32 in dilator tip 30 to aid navigation of delivery device 20 through a body lumen.

Figure 5:
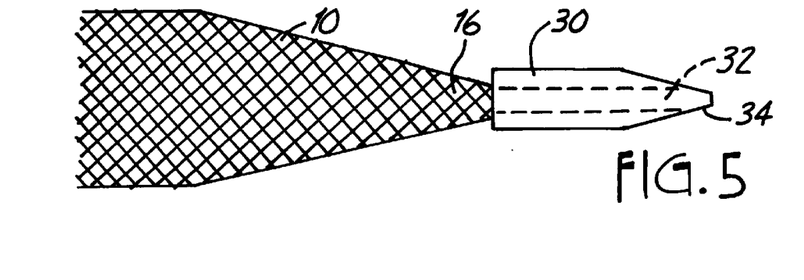
FIG. 5 is a side view of a medical device having a dilator tip attached to and extending, away from the constricted region of the medical device.

As perhaps best shown in FIG. 5, dilator tip 30 of delivery device 20 is permanently attached to occlusion device 10. Dilator tip 30 is attached using conventional means, such as adhesive or insert molding, to the distal end of the constricted region 16 of occlusion device 10 in such a manner that the dilator tip 30 extends away from constricted region 16 of occlusion device 10. The occlusion device 10 and dilator tip 30 are positioned in the medical device encompassing region 27 of outer sheath 22 so that dilator tip 30 extends beyond the distal end 23 of outer sheath 22.

Delivery device 20 can thus be used to position occlusion device 10 at a desired treatment location in a body lumen. Specifically, the distal end of the delivery device 20 is inserted in the body lumen, and the tapered surface 34 of dilator tip 30 expands the body lumen in advance of the remainder of delivery system 20. In this manner, tortuous body lumens can more easily be navigated. The position of delivery device 20 in the lumen can be tracked radiographically by monitoring the position of a conventional radiopaque marker (not shown) positioned on delivery device 20. Alternatively, the dilator tip 30 can be fabricated from a material compounded with a radiopaque filler such as bismuth subcarbonate or barium sulfate to enable visualization by radiography. When occlusion device 10 is positioned at the desired treatment location, inner tube 24 is advanced in outer sheath 22 to engage plunger 44 with the end of occlusion device 10. Outer sheath 22 is then retracted by proximally moving outer sheath 22 and manifold 25 (shown in FIG. 1) relative to occlusion device 10. Plunger 44 holds occlusion device 10 stationary while outer sheath 22 is retracted, and in this manner, occlusion device 10 is deployed from the outer sheath 22 and self expands to engage the wall of the body lumen. Occlusion device 10 is thus implanted in the body lumen at the desired treatment location. In this first embodiment, because it is attached to occlusion device 10, dilator tip 30 of delivery device 20 is deployed along with occlusion device 10 and remains implanted in the body lumen. After implantation outer sheath 22, inner tube 24, and guide wire 26 can be withdrawn from the body lumen.

While FIGS. 6–8 show a delivery device wherein the occlusion device 10 is deployed by proximal movement of outer sheath 22 relative to the occlusion device 10, other deployment techniques are contemplated. For example, outer sheath 22 can be comprised of a flexible material at its distal end that is rolled back on itself to expose an occlusion device contained within the sheath. As the outer sheath is rolled back, the occlusion device self-expands to engage the wall of the body lumen, and is thus deployed and implanted in the lumen.

Figure 9:
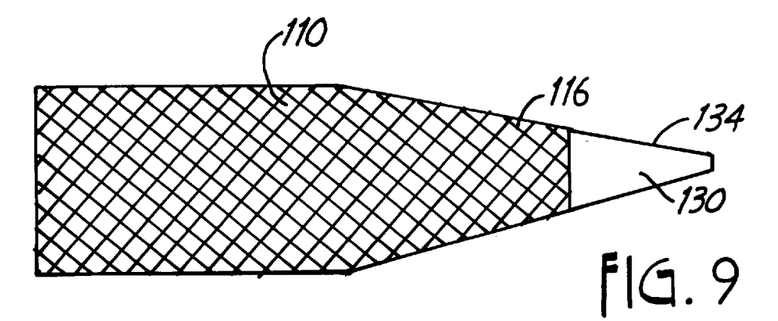
FIG. 9 is a side view of a medical device having a dilator tip attached to and coincident with the constricted region of the medical device.
Figure 10:
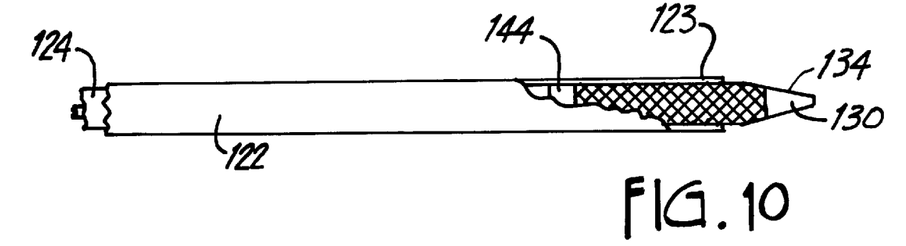
FIG. 10 is a side view of a second embodiment of a delivery device in use with the medical device shown in FIG. 9 with portions of the outer sheath of the delivery device shown in section to illustrate the medical device in the outer sheath.
Figure 11:
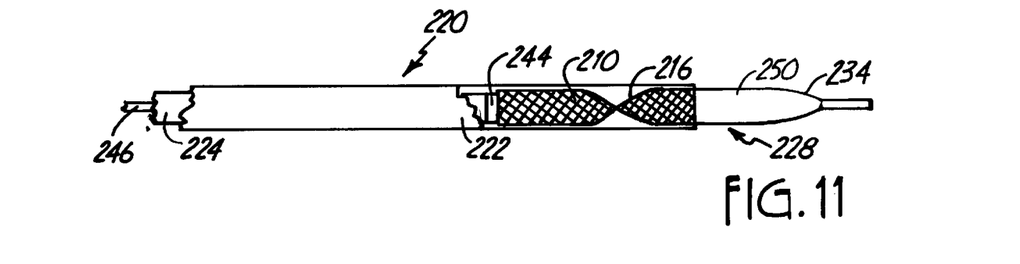
FIG. 11 is a side view of a third embodiment of a delivery device in accordance with the present invention with portions of the outer sheath shown in section to illustrate the medical device in the outer sheath and the guide member of the delivery device.
Figure 12:
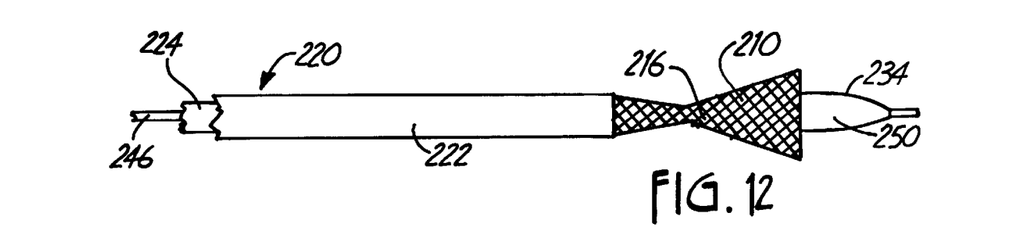
FIGS. 12–15 are side views of the third embodiment of the present invention showing the various stages of deploying a medical device having a constricted region, with portions of the medical device in FIGS. 13 and 14 being shown in section to better illustrate the deployment of the medical device.
Figure 13:
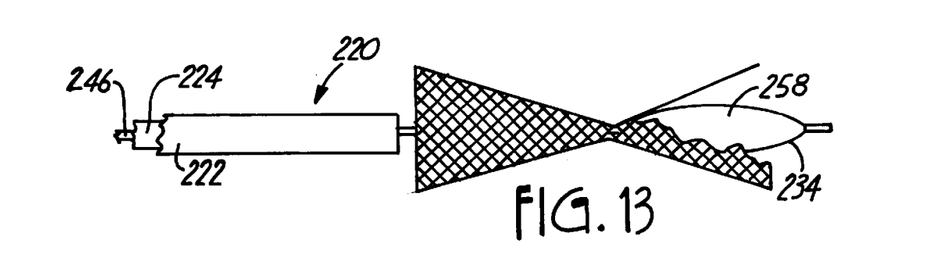
Figure 14:
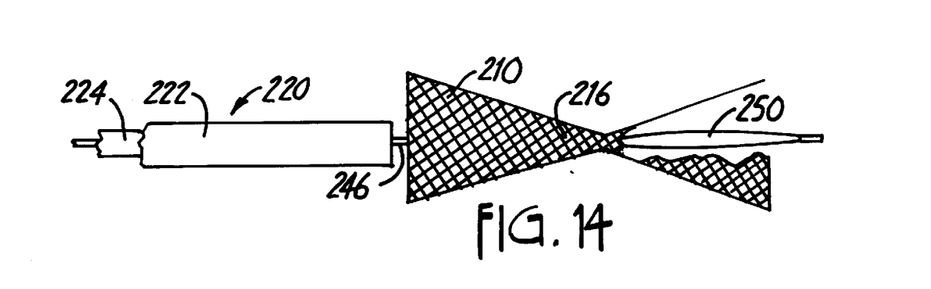
Figure 15:
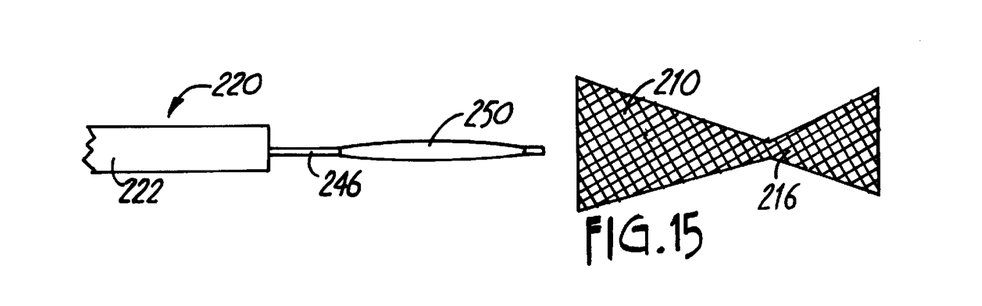

FIGS. 9 and 10 show a second embodiment of the present invention wherein similar features of the first embodiment shown in FIGS. 1 and 6–8 and described above are referred to using the same reference numeral preceded by the number "1." In this embodiment, delivery device 120 includes a conical dilator tip 130 having a tapered surface 134 and attached to the constricted region 116 of the occlusion device 110. Dilator tip 130 is coincident and integrated with the constricted region 116. Dilator tip 130 can be attached to occlusion device 110 in a conventional manner, such as with adhesive, stitching, or insert molding. Occlusion device 110 is positioned in delivery device 120 so that dilator tip 130 extends beyond distal end 123 of outer sheath 120, and is deployed by engaging plunger 144 at the end of inner tube 124 of delivery device 120 with occlusion device 110 to hold occlusion device 110 stationary as outer sheath 122 is retracted. Occlusion device 110 thus exits delivery device 120 and expands to engage the body lumen at the desired treatment location.

The dilator tip 30 of delivery device 20 and dilator tip 130 of delivery device 120 can be made from any implantable, biocompatible material, including polytetrafluoroethylene, PET, polyurethane, silicone, or metal. A preferred material for dilator tip 30 and dilator tip 130 is polycarbonate urethane.

A third embodiment of the present invention is shown in FIGS. 11–15. This third embodiment includes many of the features and components shown and described above in connection with the first and second embodiments of the present invention, and similar reference numbers preceded by the number "2" will be used to describe these features. Delivery device 220 includes an outer sheath 222, an inner tube 224 terminating in a plunger 244 at the distal end of inner tube 224, an inflation tube 246 that is concentric with both outer sheath 222 and inner tube 224, and guide member 228. Inflation tube 246 is adapted to receive and carry a fluid flow. The guide member 228 of delivery device 220 includes an inflatable balloon 250 that is positioned at the distal end of outer sheath 222 and that is fluidly coupled to inflation tube 246. Balloon 250 receives fluid through inflation tube 246 and is thus enlarged to an inflated state. In its inflated state, balloon 250 assumes a substantially elongated shape having a tapered surface 234. In this manner, balloon 250 can be used to dilate a body lumen and guide delivery device 220 through the lumen to the desired treatment location in a manner similar to that described above.

Delivery device 220 is well suited for delivering an occlusion device having a constricted region between the ends of the occlusion device, such as those shown in FIGS.

3 and 4 and described above, to a desired treatment location in a body lumen. Occlusion device 210 is carried within outer sheath 22 in a collapsed condition distally of plunger 244 of inner tube 224 and proximally of balloon 250. Balloon 250 is inflated by receiving fluid through inflation tube 246, and the delivery device 220 is then inserted in the body lumen and guided to a desired treatment location using known techniques, such as radiography. As delivery device 220 is guided to the desired treatment location, tapered surface 234 of balloon 250 dilates the body lumen in advance of the delivery system to ease navigation through the body lumen. At the desired treatment location, occlusion device 210 is deployed by advancing inner tube 224 in outer sheath 222 to engage plunger 244 with occlusion device 210, and thus hold it stationary during deployment. Sheath 222 is then retracted, and occlusion device 210 exits delivery device 220 and expands to engage the body lumen. Occlusion device 210 is thus implanted in the body lumen. After implantation, balloon 250 is deflated by removing fluid from balloon 250 through inflation tube 246. In its deflated state, balloon 250 can be withdrawn through a gap in the constricted region 216, such as exists between individual filaments of the support structure and/or the membrane of occlusion device 210. Delivery device 222 can then be withdrawn from the body lumen.

Balloon 250 of the delivery device 220 shown in FIGS. 11–15 can be formed from any known balloon material, including nylon, PET, polyethylene, polyurethane, and polyvinylchloride. The preferred material for ballon 250 is Nylon 12.

The delivery device shown and described above provides many advantages over conventional delivery devices. Specifically, the delivery device provides a guide member that dilates a body lumen in advance of the delivery device, and thus eases navigation through the lumen, yet can efficiently be used with a medical device having a constricted region. In addition, a delivery device in accordance with the present invention contains few moving parts, and thus is efficient to manufacture and to use.

Figure 16:
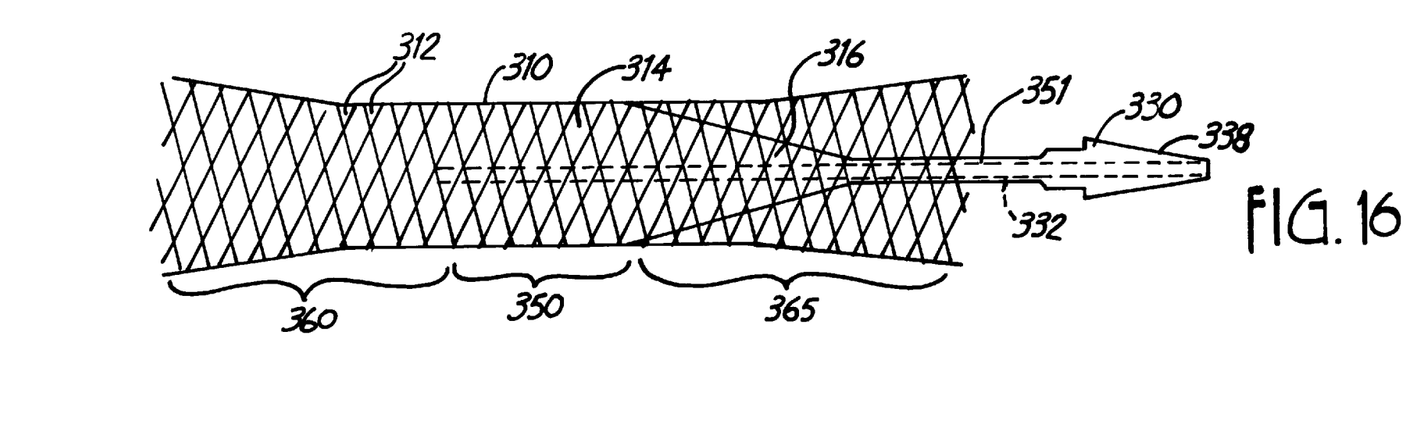
FIG. 16 is a side view of a medical device having a dilator tip integral with the membrane of the medical device.
Figure 19:
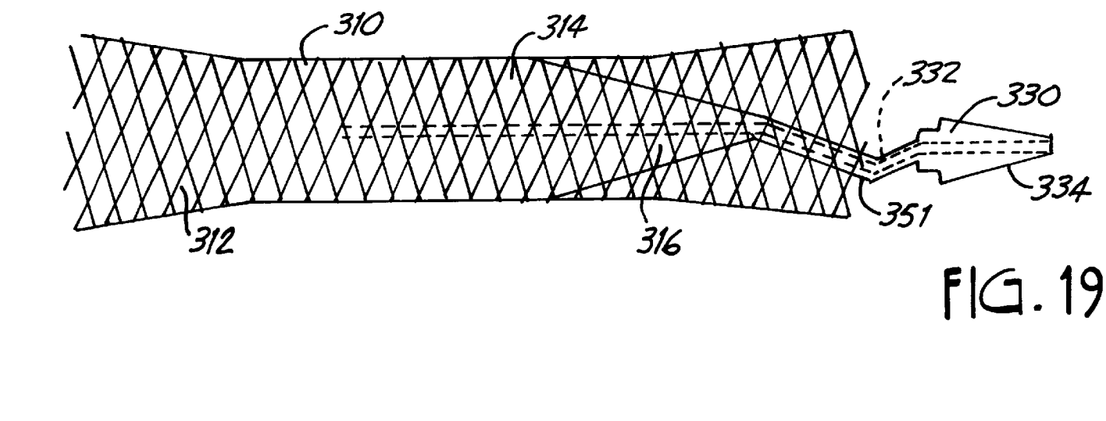
FIG. 19 is a side view of the medical device of FIG. 16 wherein the constricted region is pinched upon deployment of the device to better occlude fluid flow.

FIGS. 16 and 19 show another embodiment 310 of an occlusion device which can be deployed by the present invention. Occlusion device 310 is comprised of a self-expanding support structure 312 and a membrane 314. Self-expanding support structure 312 is comprised of a plurality of helically braided wires 312, which are preferably formed of nitinol, stainless steel, Elgiloy, or the like. Alternatively, self-expanding support structure 312 can be made by machining diamond-shaped windows with a laser i or by EDM means from a thin-walled tube to form struts that comprise the self-expanding support structure 312. Membrane 314 is attached to the inner surface of support structure 312. Specifically, membrane 314 lines and is integrally attached to a center portion 350 of support structure 312. Alternatively,membraine 314 can be sewn to support structure 312. Membrane 314 includes a constricted region 316 that terminates at a cylindrical section 351. Cylindrical section 351 is integrally attached at its distal end to a dilator tip 330, which includes tapered surface 334. Membrane 314 can contain a guidewire channel 332 (shown in phantom) concentric within membrane 314.

Occlusion device 310 includes regions 360 and 365, which are free from attachment to membrane 314. Regions 360 and 365 thus enable flow through and across the regions, and across membrane 314 in region 365, if occlusion device 310 is placed across a branch vessel in a body lumen wherein maintenance of fluid flow is desired. Regions 360 and/or 365 can of course contain membranes to occlude side branch vessels if required.

As perhaps best shown in FIG. 19, the cylindrical section 351 of constricted region 316 of occlusion device 310 can be bent or kinked to pinch off the guidewire channel 332 to hasten occlusion of the body lumen in which occlusion device 310 is implanted. As described above, membrane 314 is flexible, and can be formed of a sufficiently thin walled material such as those described above to permit the bending of cylindrical section 351 under normal fluid flow forces. Alternatively, the guidewire can be adapted to form a pinch in cylindrical section 351 as it is withdrawn from occlusion device 310, or membrane 314 can be formed of a material that softens once occlusion device 310 is implanted in the body to pinch off guidewire channel 332.

Figure 17:
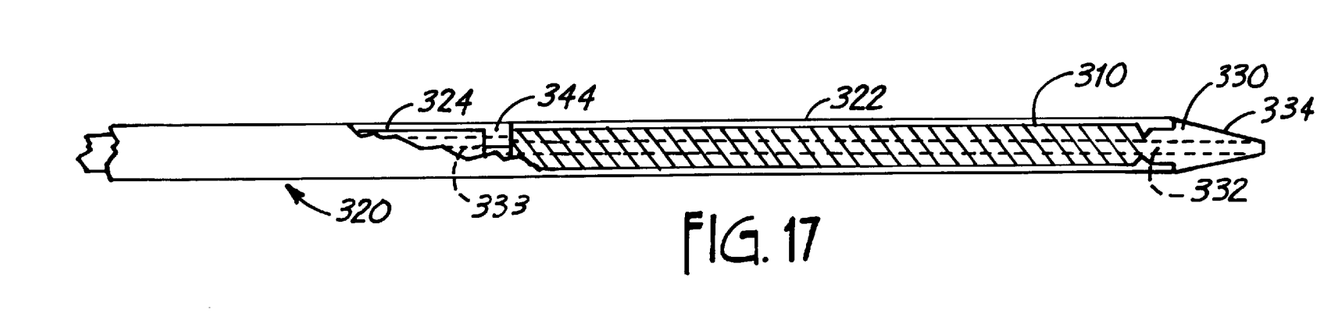
FIG. 17 is a side view of a fourth embodiment of a delivery device in use with the medical device shown in FIG. 16 with portions of the outer sheath of the delivery device shown in section to illustrate the medical device in the outer sheath.

FIG. 17 shows a delivery device 320 for delivering and implanting occlusion device 310 at a desired location within a body lumen. Delivery device 320 includes an outer sheath 322 and an inner tube 324 terminating at its distal end in a plunger 344. Occlusion device 310 is contained in its compressed state within outer sheath 322 at a distal end of outer sheath 322. Dilator tip 330 extends distally from the distal end of outer sheath 322, and is adapted to dilate a body lumen and guide the delivery device 320 through the lumen as it is advanced in the body lumen. A guide wire can be inserted through channel 322 in medical device 310 and throughout the length of delivery device 320 through a channel 333 to facilitate maneuvering in tortuous body lumens.

Medical device 310 is deployed from delivery device 320 in a manner similar to that described above. Specifically, occlusion device 310 is deployed by pushing inner tube 324 so that plunger 344 butts up against the proximal end of occlusion device 310. Inner tube 324 is then held firmly in place while outer sheath 322 is retracted. In this manner, occlusion device 310 self expands as it exists the outer sheath 322, and is thus implanted in the body lumen to occlude fluid flow through the body lumen.

Figure 18:
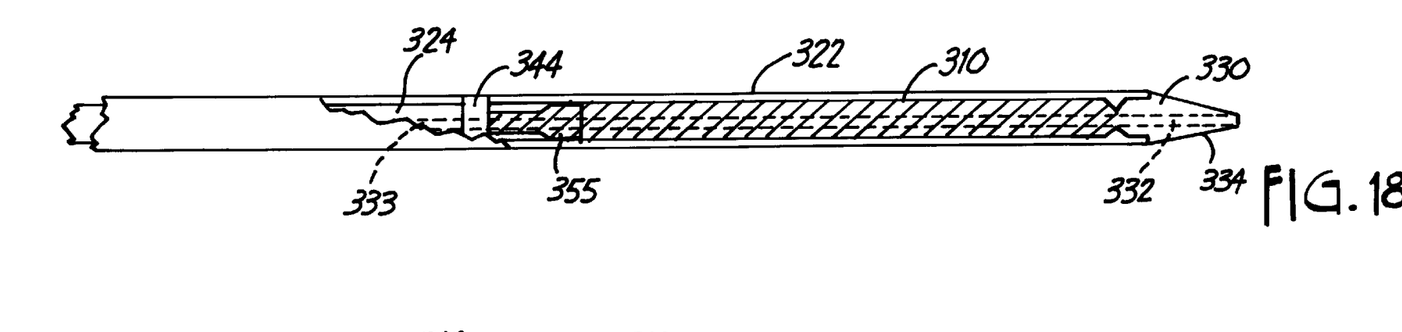
FIG. 18 is a side view of the delivery device shown in FIG. 17 further including a reconstrainment member, with portions of the outer sheath of the delivery device shown in section to illustrate the medical device in the outer sheath.

As is shown in FIG. 18, the delivery device 320 can include a reconstrainment member 355 that enables the occlusion device 310 to be reconstrained into its compressed state by loading occlusion device 310 back into outer sheath 322 prior to being totally deployed in the event occlusion device 310 is incorrectly placed or located in the body lumen. Reconstrainment members are generally known, and are described in U.S. Pat. No. 5,026,377 to Burton et al. Reconstrainment member 355 can be attached to plunger 344, and is positioned within the end of occlusion device 310. Reconstrainment member 355 is sized and shaped to frictionally engage the support structure of occlusion device 310 when occlusion device 310 is in its compressed state. Toward this end, reconstrainment member is preferably constructed of a material that has a sufficiently high coefficient of friction on its outer surface to prevent relative motion between occlusion device 310 and reconstrainment member 355. Suitable materials for reconstrainment member 355 include silicone rubber and polyurethane. Because reconstrainment member 355 frictionally engages occlusion device 310, reconstrainment member 355 allows the occlusion device 310 to be drawn back into outer sheath 322 prior to complete deployment of occlusion device 310 by extending outer sheath 322 relative to occlusion device 310. Extending outer sheath 322 re-compresses occlusion device 310, and loads it back into delivery device 320. Reconstrainment member 355 can include a hollow chamber coincident with chamber 333 of device 320 to permit the insertion of a guidewire through reconstrainment member 355.

In addition to the advantages of the present invention described above, the delivery device and medical devices of FIGS. 16–19 provide additional advantages over conventional delivery systems. Because the ends of the support structure of the occlusion devices shown in FIGS. 16 and 19 are free from attachment to the fluid-flow occluding membrane, the ends of the support structure flare out. The flared ends of the support structure thus prevent migration of the occlusion device in both prograde and retrograde flow through a body lumen in which the occlusion device is implanted. In addition, an occlusion device having bare metal on either end and with minimum membrane material in a center region of the occlusion device can be factory loaded into a delivery device without the occlusion device taking a permanent set with time. Occlusion devices having voluminous membranes, when stored for a long periods of time, assume a set in the compressed state of the occlusion device, and thus may not readily open in a body lumen upon deployment in the lumen. Occlusion device having a membrane such as those shown in FIGS. 16 and 19 and described above overcome such a shortcoming, and thus allow the occlusion device to be factory loaded into a delivery device. Such a medical device and delivery device is particularly helpful to a practitioner.

Although the present invention has been described with reference to preferred embodiments, those skilled in the art will recognize that changes may be made in form and detail without departing from the spirit and scope of the invention.

What is claimed is:

1. A combination fluid flow-occluding medical device and delivery device, the delivery device adapted to be advanced in a body lumen to deliver the medical device to a desired location in the body lumen and to deploy the medical device at the desired location, comprising:

a radially expandable fluid flow-occluding medical device having a constricted region, the constricted region substantially preventing the passage of fluid through the body lumen when the device is deployed;

an outer sheath having a distal end, the medical device being positioned within the outer sheath in a radially compressed state;

an actuator for deploying and implanting the medical device at the desired location in the body lumen; and a guide member attached to the fluid-flow occluding medical device and extending beyond the distal end of the outer sheath when the medical device is positioned within the outer sheath for dilating the body lumen and guiding the delivery device through the body lumen as the delivery device is advanced in the body lumen.

2. The combination medical device and delivery device of claim 1, wherein the actuator includes an inner tube positioned within the outer sheath, the inner tube terminating in an end adjacent a proximal end of the medical device.

3. The combination medical device and delivery device of claim 2, wherein the guide member includes a dilator tip having an outwardly sloping surface for dilating the body lumen as the delivery device is advanced in the body lumen.

4. The combination medical device and delivery device of claim 3 wherein the dilator tip is attached to the constricted region of the medical device and extends away from the constricted region of the medical device.

5. The combination medical device and delivery device of claim 4, further including a reconstrainment member attached to the end of the inner tube and positioned within the medical device for reconstraining the medical device prior to complete deployment of the medical device from the delivery device.

6. The combination medical device and delivery device of claim 3 wherein the dilator tip is attached to the constricted region of the medical device and is coincident with at least a portion of the constricted region.

* * * * *